United States Patent
Lee et al.

(10) Patent No.: US 8,993,340 B2
(45) Date of Patent: Mar. 31, 2015

(54) DEVICE AND METHOD OF SEPARATING CELLS BY USING MAGNETIC FORCE

(75) Inventors: Hun-joo Lee, Hwaseong-si (KR); Jeong-gun Lee, Seoul (KR); Mi-jeong Song, Suwon-si (KR); Jong-myeon Park, Incheon (KR); Tae-seok Sim, Seoul (KR); Min-seok S. Kim, Daejeon (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1046 days.

(21) Appl. No.: 13/051,251

(22) Filed: Mar. 18, 2011

(65) Prior Publication Data
US 2012/0077267 A1    Mar. 29, 2012

(30) Foreign Application Priority Data

Sep. 28, 2010   (KR) .................. 10-2010-0093805

(51) Int. Cl.
*G01N 1/28*  (2006.01)
*C12N 5/00*  (2006.01)
(Continued)

(52) U.S. Cl.
CPC .......... *C12M 47/04* (2013.01); *B01L 3/502753* (2013.01);
(Continued)

(58) Field of Classification Search
CPC ............ G01N 1/4077; G01N 2001/4077; G01N 35/0098; B01L 3/502715; B01L 3/502753; B01L 3/502761; B01L 2300/0864; C12M 47/04; C12M 1/266; B03C 1/02; B03C 1/10; B03C 1/12; B03C 1/14; B03C 1/145
See application file for complete search history.

(56) References Cited

U.S. PATENT DOCUMENTS 6,467,630 B1 * 10/2002 Zborowski et al. ........... 209/459
2006/0024824 A1    2/2006 Woodside et al.
(Continued)

FOREIGN PATENT DOCUMENTS

KR    1020060039710 A    5/2006
KR    1020080022025 A    3/2008
(Continued)

OTHER PUBLICATIONS

Pamme, Nicole. "Magnetism and microfluidics." Lab on a Chip (2006) 6 24-38.*

*Primary Examiner* — Christopher A Hixson
(74) *Attorney, Agent, or Firm* — Leydig, Voit & Mayer, Ltd.

(57) ABSTRACT

A cell separation device includes a channel or chamber in which a sample flows or moves, the sample including target cells marked with magnetic particles, and non-target cells, and a magnet which generates a magnetic first force in a first direction with respect to the sample within the channel or chamber. The channel or chamber of the cell separation device is applied with a second force in a second direction opposite to the first direction of the magnetic force. According to the cell separation device and a method of separating cells, the target cells move in the first direction by the magnetic force, and the non-target cells move in the second direction by the second force, by simultaneously applying the magnetic force and the second force in opposing directions, thereby separating the target cells from the non-target cells.

20 Claims, 6 Drawing Sheets

(51) Int. Cl.
  *C12M 1/00* (2006.01)
  *B01L 3/00* (2006.01)
  *B03C 1/14* (2006.01)
  *G01N 1/40* (2006.01)
  *C12M 1/26* (2006.01)
  *B03C 1/02* (2006.01)

(52) U.S. Cl.
  CPC ............ *B03C 1/14* (2013.01); *B01L 3/502761* (2013.01); *G01N 1/4077* (2013.01); *B03C 1/145* (2013.01); *C12M 1/266* (2013.01); *B03C 1/02* (2013.01); *B01L 2300/0864* (2013.01)
  USPC ......................................................... 436/174

(56) References Cited

U.S. PATENT DOCUMENTS

| | | |
|---|---|---|
| 2008/0187472 A1 | 8/2008 | Ahn et al. |
| 2008/0302726 A1* | 12/2008 | Moller et al. ................. 210/661 |
| 2009/0014360 A1* | 1/2009 | Toner et al. ................... 209/208 |
| 2009/0078614 A1 | 3/2009 | Varghese et al. |
| 2010/0093052 A1 | 4/2010 | Chalmers et al. |
| 2010/0227379 A1* | 9/2010 | Wo et al. ....................... 435/261 |

FOREIGN PATENT DOCUMENTS

| | | |
|---|---|---|
| KR | 1020100013403 A | 2/2010 |
| WO | WO 2005059929 A2 * | 6/2005 |
| WO | WO 2008110019 A1 * | 9/2008 |

* cited by examiner

DEVICE AND METHOD OF SEPARATING CELLS BY USING MAGNETIC FORCE

CROSS-REFERENCE TO RELATED APPLICATIONS

This application claims priority to Korean Patent Application No. 10-2010-0093805, filed on Sep. 28, 2010, and all the benefits accruing therefrom under 35 U.S.C. §119, the disclosure of which is incorporated herein in its entirety by reference.

BACKGROUND

1. Field

Provided are a device and a method of separating cells by using a magnetic force, and more particularly, a device and a method of efficiently separating target cells from other cells by simultaneously generating a magnetic force, and a force applied in the opposite direction of the magnetic force.

2. Description of the Related Art

A cell is a basic unit of an animal's body, and organs in the body include different types of cells. In general, biopsies have been used to diagnose various diseases. However, due to the recent improvement in the accuracy of cytology, diseases can be simply and precisely diagnosed by using cytology. Particularly, as patients may avoid unnecessary biopsies, a lot of attention has been paid to the use of cytology for precise diagnosis.

A target cell needs to be extracted from a sample for cytology. A target cell can be separated from a solid tissue by figuring out the location of the target cell using a microscope. However, since bodily fluid (e.g., blood) contains various cells, it is difficult to separate a target cell therefrom. Since various cells or substances related to diseases are mixed in blood, it is essential to separate a target cell from a fluid such as blood in which various cells are mixed, and remove undesired cells.

In particular, research into cancer cells in blood has received much attention. Malignant tumor-related deaths are generally caused by metastasis by which tumors spread to distant organs or tissues. Accordingly, early detection of tumors and monitoring the growth of the tumors are important for successfully treating cancers. Histopathology has been used to diagnose cancers. Histopathology is a method used for analyzing tumors using a sample from a living tissue. Such a histopathological approach requires a direct observation of tumor cells. However, tumors may not exist at a location of a tissue selected to obtain a living sample. In addition, data from only a specific location in the living sample can be obtained, and thus it is difficult to know whether tumors are metastasized to other locations.

It is known that cell circulating tumor cells ("CTCs") can be detected in patients before tumor cells are initially detected. Thus, the CTCs may be used for early detection and prediction of cancers. Furthermore, since most cancers are metastasized via blood, the CTCs may be used as a marker for the metastasis of cancers. In addition, if the CTCs are detected after removing cancer cells by surgery, a cancer relapse may be detected. However, it is difficult to detect the existence and number of the CTCs since the content of the CTCs is very low in blood and the CTCs are fragile. Therefore, there is a need to develop a highly sensitive diagnosis method for detecting CTCs, cancer cells, or cancer stem cells contained in a patient's body. For this, a method of efficiently separating tumor cells contained in a biological sample and a device therefore are required.

Recently, magnetic separation techniques using a magnetic force have been used in the fields of medical & bio technology in various ways. Much attention has been paid to magnetic separation techniques due to scalability, efficiency, simplicity, simple conditions, automation, and low costs. According to magnetic separation techniques, a sample is cultured using magnetic particles that have high affinity to a target material and are sensitive to a magnet. In a separation method using such a magnetic force, micro particles or beads having a diameter in the range of about 10 nanometers (nm) to about 20 micrometers (μm) are used.

According to general magnetic separation techniques, when only a magnetic force of the magnet is applied, the target materials or cells which are marked with the magnetic particles are pulled toward the magnet by the magnetic force, however, other cells also move by a flow generated while cells marked with magnetic particles move due to the magnetic force, and may be trapped. Thus, a cell separation ratio may decrease and false-positiveness may increase when only the magnetic force is applied. Furthermore, since the other cells undesirably move by the flow generated while marked cells move when only a magnetic force of the magnet is applied, a separate washing process is required to remove non-specifically bound cells, and thus the target cells may also be washed or cell membranes may be damaged by shear stress generated during the washing process, thereby increasing cell loss.

SUMMARY

Provided are a device and a method of efficiently separating target cells from other cells by simultaneously generating a magnetic force, and a force applied in the opposite direction of the magnetic force.

Additional aspects will be set forth in part in the description which follows and, in part, will be apparent from the description, or may be learned by practice of the presented embodiments.

Provided is a cell separation device including a channel having a curved shape in a plan view, and in which a sample flows, the sample comprising target cells marked with magnetic particles, and non-target cells, a sample inlet connected to a first end of the channel, a first sample outlet and a second sample outlet respectively connected to a second end of the channel opposing the first end, and a magnet adjacent to an outer circumference of the channel. The magnet generates a magnetic force with respect to the sample.

In an embodiment, the channel may have a circular or oval shape.

In an embodiment, the channel may have a spiral shape that is a planar curve emanating from a central point, and getting progressively farther away from the central point as it revolves around the central point.

In an embodiment, the sample inlet may be connected to the first end of the channel at the central point, and the first and second sample outlets are connected to the second end of the channel at an outer point of the spiral shape.

In an embodiment, the magnet may include a single long circular magnet that parallels the outer circumference of the channel.

In an embodiment, an inner distance within the channel may be greater than a diameter of cells contained in the sample that flows in the channel by about 2 to about 20 times.

In an embodiment, the magnetic force generated by the magnet may be greater than an inertial force generated while a sample flows in the curved channel.

Provided is a cell separation device including a chamber in which a sample flows, the sample including target cells marked with magnetic particles, and non-target cells, a magnet disposed at an upper portion of the chamber, the magnet generating a magnetic force with respect to the sample, and a rotation member aligned on a rotation axis and connected to the upper portion of the chamber. The rotation member is disposed closer to the magnet at the upper portion of the chamber and farther from a bottom surface of the chamber, and the magnetic force generated by the magnet is greater than a centrifugal force generated while the chamber rotates with respect to the rotation axis.

In an embodiment, the magnet may have a protective coating on a surface thereof in order to prevent the magnet from being damaged by the sample.

In an embodiment, the magnet may have a sloping side in contact with the sample.

Provided is a cell separation device including a disc that rotates with respect to a central rotation axis, a chamber disposed on an upper surface of the disc and in which a sample flows, the sample including target cells marked with magnetic particles, and non-target cells, and a magnet disposed in the chamber and generating a magnetic field with respect to the sample. The magnet is disposed between the chamber and the rotation axis of the disc, and the magnetic force generated by the magnet is greater than a centrifugal force generated in the chamber when the disc rotates with respect to the central rotation axis.

In an embodiment, the chamber may be disposed on the disc such that a lengthwise direction of the chamber is aligned with a radial direction of the disc.

In an embodiment, a plurality of the chamber may be disposed on the disc at equal intervals according to an azimuth angle.

Provided is a cell separation device including a chamber in which a sample flows, the sample including target cells marked with magnetic particles, and non-target cells, a sample supply tube that penetrates a top surface of the chamber and is disposed in the chamber, a magnet disposed in the chamber to surround the sample supply tube and generating a magnetic force with respect to the sample, and a sample outlet connected to an upper side of the chamber. The magnetic force generated by the magnet is greater than a centrifugal force generated when a sample rotates in the chamber with respect to the sample supply tube.

In an embodiment, the chamber may have a conic shape with a sloping side which has a relatively wide top surface and a relatively narrow bottom surface.

In an embodiment, the sample supply tube includes a first end protruding from the top surface of the chamber and into which the sample is introduced, and a second end of the sample supply tube disposed to be close to the bottom surface of the chamber.

In an embodiment, the sample supply tube may be disposed at a central region of the chamber.

In an embodiment, the magnet may be a cylindrical magnet that surrounds the sample supply tube.

Provided is a cell separation device including a cylindrical magnet, a channel that helically winds around the magnet and in which a sample flows, the sample including target cells marked with magnetic particles, and non-target cells, the cylindrical magnet generating a magnetic force with respect to the sample, a sample inlet connected to a first end of the channel, and a first sample outlet and a second sample outlet respectively connected to a second end of the channel opposite the first end. The magnetic force generated by the magnet is greater than a centrifugal force generated when a sample flows in the helical channel and rotates around the magnet.

In an embodiment, the channel may be a cylindrical tube winding multiple times around the magnet.

In an embodiment, a diameter of the channel may be greater than a diameter of cells contained in the sample by at least 20 times.

Provided is a method of separating cells including preparing a sample including target cells marked with magnetic particles and non-target cells, applying a magnetic force to the sample in a first direction, applying a second force other than the magnetic force to the sample in a second direction opposite to the first direction, and moving the target cells marked with the magnetic particles in the first direction and the non-target cells in the second direction.

In an embodiment, the magnetic force may be greater than the second force.

In an embodiment, the second force may include at least one selected from the group consisting of an inertial force, a Dean drag force, and a centrifugal force.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
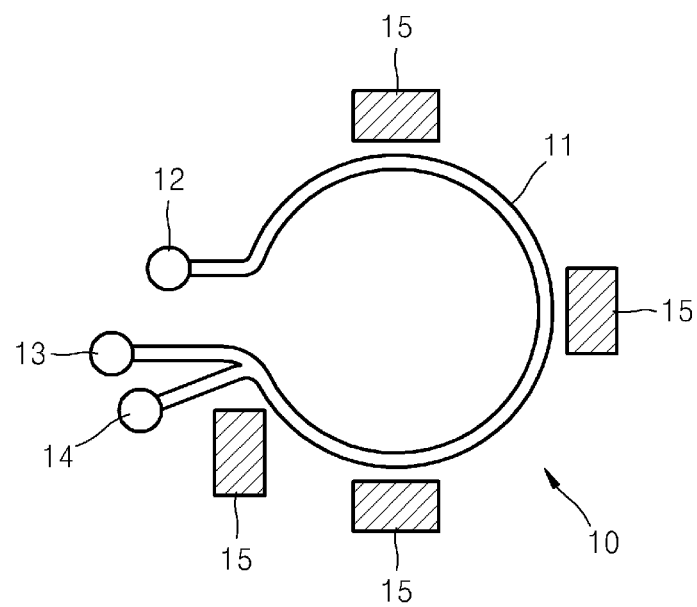
FIG. 1 schematically illustrates an embodiment of a cell separation device, according to the present invention.

Reference will now be made in detail to embodiments, examples of which are illustrated in the accompanying drawings. In this regard, the present embodiments may have different forms and should not be construed as being limited to the descriptions set forth herein. Accordingly, the embodiments are merely described below, by referring to the figures, to explain aspects of the present description. In the drawings, like reference numerals refer to like elements, and the size of each component is exaggerated for convenience and clarity.

It will be understood that when an element or layer is referred to as being "on" or "connected to" another element or layer, the element or layer can be directly on or connected to another element or layer or intervening elements or layers. In contrast, when an element is referred to as being "directly on"

or "directly connected to" another element or layer, there are no intervening elements or layers present. As used herein, connected may refer to elements being physically and/or fluidly connected to each other.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the invention.

Spatially relative terms, such as "lower," "under," "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, a device and method of separating cells by using a magnetic force will be described.

FIG. 1 schematically illustrates an embodiment of a cell separation device 10 according to the present invention. Referring to FIG. 1, the cell separation device 10 according to the present embodiment includes a channel 11 having a curved shape in a plan view, a sample inlet 12 that is connected to a first end of the channel 11, a first sample outlet 13 and a second sample outlet 14 which are respectively connected to a second end of the channel 11 opposite to the first end, and at least one magnet 15 that is aligned along an outer circumference of the channel 11. In one embodiment, for example, the channel 11 may have a circular shape as shown in FIG. 1, or an oval shape. In this regard, a central region of a curvature of the curved channel 11 in the plan view may be regarded as inside the channel 11, and a region opposite to the central region of the curvature of the channel 11 may be regarded as outside the channel 11.

The sample inlet 12, the first sample outlet 13 and the second sample outlet 14 are in fluid communication with the channel 11, and collectively form a continuous, single and unitary indivisible fluid path with the channel 11.

As illustrated in FIG. 1, the cell separation device 10 may include a plurality of the magnet 15 aligned along an outer circumference of the channel 11. Each of the magnets 15 may be disposed along an outer circumference of the channel 11 (e.g., at the outside of the channel 11). The magnet 15 may be a permanent magnet, or an electromagnet that generates a magnetic force only when activated.

In the cell separation device 10 according to the present embodiment, a sample including target cells may be supplied to the channel 11 via the sample inlet 12. The sample may be a liquid sample such as blood obtained from a subject. In order to separate the target cells using the magnetic force, the target cells contained in the sample may be marked with magnetic particles. The sample supplied to the channel 11 via the sample inlet 12 flows in the channel 11. While the sample flows in the channel 11, the following three types of forces may be simultaneously applied to the cells contained in the sample. That is, a Dean drag force that is generated by resistance of a fluid while the sample flows in the channel 11, an inertial force that is generated while a sample flows along the curved channel 11, and a magnetic force that is generated by the magnet 15, may be applied to the cells in the sample.

When a height of the channel 11 (e.g., a maximum distance between opposing inner walls or edges of the channel 11) is greater than a diameter of the cells contained in the sample by about 2 to 20 times, the Dean drag force is generated which causes the cells to move along the edges of the channel 11. Due to the Dean drag force, the cells rarely exist in a central region of the channel 11. The inertial force is applied toward the center of the curvature when the sample flows in the curved channel 11 so that the cells move along a relatively inner edge of the channel 11. The magnetic force generated by the magnet 15 that is disposed along the outer circumference of the channel 11 is applied in the opposite direction of the center of the curvature so that the cells marked with the magnetic particles move along a relatively outer edge of the channel 11.

Figure 2:
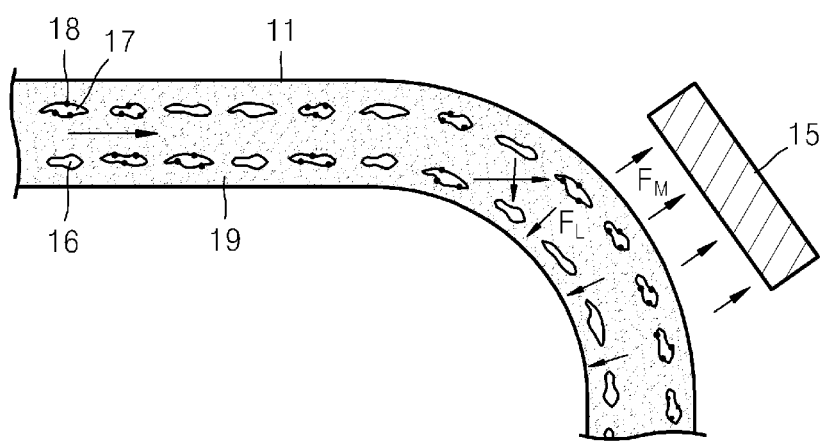
FIG. 2 is a diagram for explaining a principle of separating target cells from other cells in the cell separation device of FIG. 1.

FIG. 2 is a diagram for explaining a principle of separating target cells in a sample from the other cells in the sample, by the forces in the cell separation device of FIG. 1. Referring to FIG. 2, a liquid sample 19 is assumed to move from left to right in the channel 11. In the left portion of the channel 11, target cells 17 and other cells 16 of the sample 19 move along both edges of the channel 11 due to the Dean drag force. In the channel 11, the target cells 17 marked with magnetic particles 18 and the other cells 16 are mixed and have not been separated from each other, yet. FIG. 2 shows the channel 11 having a linear section to describe migration of cells due to the Dean drag force. However, the channel 11 is not required to have the linear section.

As shown in the right portion of FIG. 2, when the target cells 17 and the other cells 16 flow in a curved section of the channel 11, an inertial force $F_L$ that is applied toward the center of the curvature is applied to the target cells 17 and the other cells 16. Since the magnet 15 is disposed along the outer circumference of the channel 11, a magnetic force $F_M$ that is applied in an opposite direction to that of the center of the curvature is applied to the target cells 17 marked with the magnetic particles 18. However, the magnetic force $F_M$ does not affect to the other cells 16 that are not marked with the magnetic particles 18. If the magnetic force $F_M$ is greater than the inertial force $F_L$, the target cells 17 marked with the magnetic particles 18 are pulled by the magnetic force $F_M$ to move along the relatively outer edge of the channel 11 as shown in FIG. 2. On the other hand, the other cells 16 which are not influenced by the magnetic force $F_M$ move along the relatively inner edge of the channel 11 by the inertial force $F_L$ as shown in FIG. 2. Accordingly, the target cells 17 and the other cells 16 move in the channel 11 and are separated from each other.

Referring back to FIG. 1, an outlet of the channel 11 is connected to the first sample outlet 13 and the second sample outlet 14, respectively. As shown in FIG. 1, while the first sample outlet 13 is directly connected to the relatively inner edge of the channel 11, the second sample outlet 14 is directly connected to the relatively outer edge of the channel 11. Thus, the target cells 17 marked with the magnetic particles 18 that move along the relatively outer edge of the channel 11 may be output via the second sample outlet 14, and the other cells 16 not marked with the magnetic particles 18 that move along the relatively inner edge of the channel 11 may be output via the first sample outlet 13.

As described above, according to the present embodiment, the target cells 17 move due to the magnetic force, and the other cells 16 may move in the opposite direction to the target cells 17 by simultaneously applying the magnetic force and a second force in the opposite direction to the magnetic force (e.g., the inertial force and Dean drag force, or a centrifugal force that will be described later) to the channel 11 in which the sample 19 flows. Accordingly, a separation ratio of the target cells 17 may be increased, and false-positiveness caused by the other cells 16 may be reduced. In addition, with the increase in the separation ratio of the target cells 17, a washing process is not required, and thus cell loss or cell lysis caused by the washing may be reduced or effectively prevented.

Figure 3:
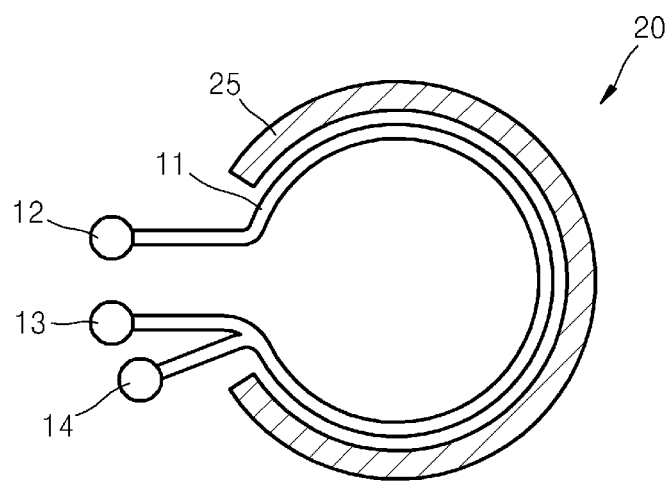
FIG. 3 schematically illustrates another embodiment of a cell separation device, according to the present invention.

FIG. 1 shows four magnets 15 disposed along the outer circumference of the channel 11. However, the number of the magnets 15 is not limited thereto. In order to increase portions of the channel 11 to which the magnetic force is applied by the magnet 15, more magnets 15 may be disposed along the outer circumference of the channel 11. Alternatively, a single, long magnet may be disposed to surround the channel 11. In one embodiment, for example, FIG. 3 schematically illustrates another embodiment of a cell separation device 20 according to the present invention. FIG. 3 shows the cell separation device 20 including a single, continuous and unitary long circular magnet 25 that consecutively surrounds the outer circumference of the channel 11. That is, the single long circular magnet 25 is substantially parallel to the curved channel 11, and extends from an inlet of the channel 11 to the outlet of the channel 11. The other configurations of the cell separation device 20 are the same as those of the cell separation device 10 shown in FIG. 1.

Figure 4:
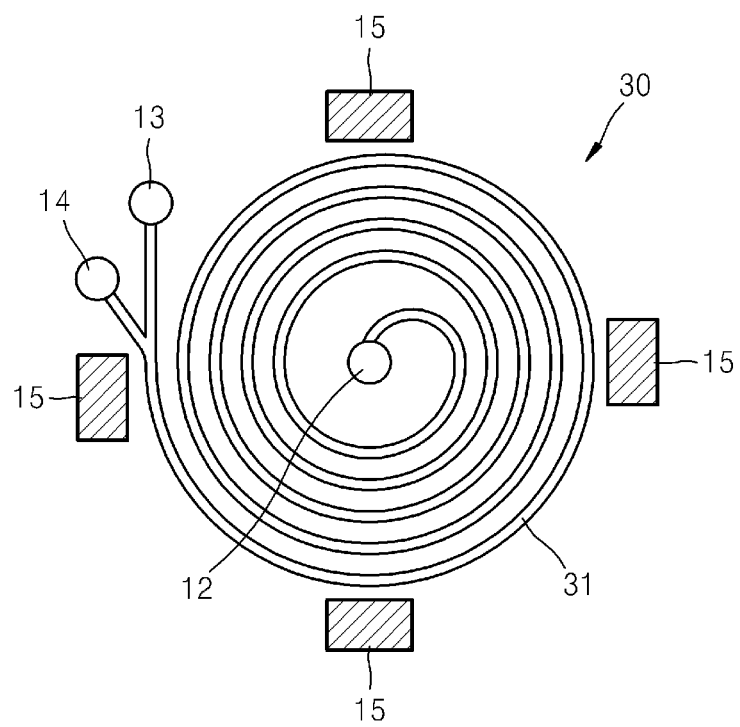
FIG. 4 schematically illustrates another embodiment of a cell separation device, according to the present invention.

In addition, in order to precisely separate the target cells 17 in the sample 19 from the other cells 16 in the sample 19, the channel 11 should be sufficiently long. Although FIG. 1 shows the circular channel 11, the shape of the channel 11 may vary to be longer within the same area. In one embodiment, for example, FIG. 4 schematically illustrates another embodiment of a cell separation device 30 according to the present invention. The cell separation device 30 shown in FIG. 4 may include a channel 31 having a spiral shape in the plan view, that is a planar curve which emanates from a central point, getting progressively farther away as it revolves around the central point. As shown in FIG. 4, since the channel 31 has a spiral shape, the length of the channel 31 may be greater than that of the channel 11 shown in FIG. 1, even though they occupy the substantially same planar area. Referring to FIG. 4, a sample inlet 12 is connected to an inner central (first) end of the channel 31, and first and second sample outlets 13 and 14 are connected to an outer (second) end of the channel 31.

Figure 5A:
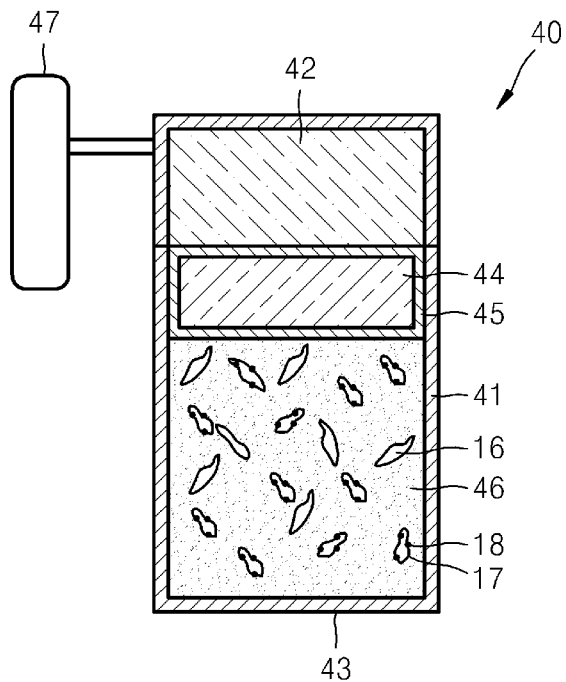
FIG. 5A schematically illustrates another embodiment of a cell separation device, according to the present invention.

FIG. 5A schematically illustrates another embodiment of a cell separation device 40 according to the present invention. The cell separation device 40 shown in FIG. 5A includes a chamber 41 that contains a sample 46, a magnet 44 that is disposed at an upper portion of the chamber 41 and a rotation member 47 that is aligned on a vertical rotation axis. The rotation member 47 is connected to an upper portion of the chamber 41. According to the present embodiment, as shown in FIG. 5A, the rotation member 47 aligned on the vertical rotation axis is disposed closer to the magnet 44 at the upper portion of the chamber 41 and farther from the bottom surface 43 of the chamber 41. In addition, the chamber 41 may further include a cover 42 that seals the upper portion of the chamber 41 to prevent the sample 46 from leaking. In this regard, the magnet 44 may be attached to the bottom surface of the cover 42, and the rotation member 47 that is aligned on the rotation axis may be connected to the top surface of the cover 42. In one embodiment, for example, the rotation member 47 may be connected to the top surface of the cover 42 via a hinge so as to be bendable with respect to the chamber 41. If the magnet 44 directly contacts with the liquid sample 46, it may be damaged, for example, rusted, by the sample 46. Accordingly, in order to prevent damage to the magnet 44, the present invention may include outer surfaces of the magnet 44 having a protective coating 45 thereon. In one embodiment, for example, the protective coating 45 may include a material that reduces or effectively prevents the infiltration of the sample 46, such as a polymer or glass.

Figure 5B:
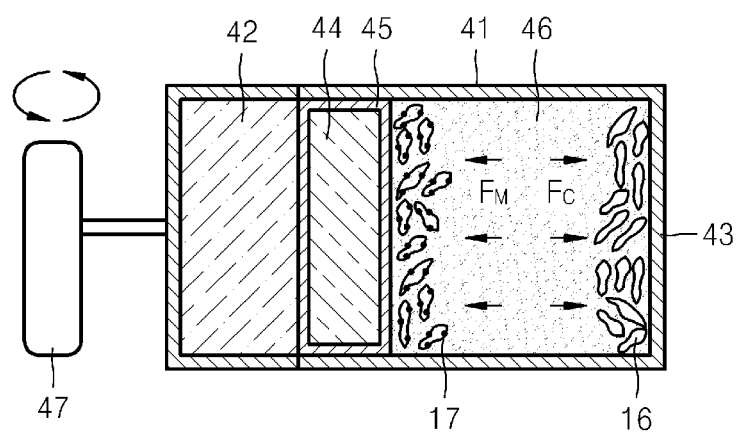
FIG. 5B is a diagram for explaining a principle of separating target cells from other cells in the cell separation device of FIG. 5A.

Principles of operation of the cell separation device 40 shown in FIG. 5A will be described with reference to FIG. 5B. Referring to FIG. 5B, the chamber 41 is filled with the sample 46, and the chamber 41 is rotated with respect to the rotation axis of the rotation member 47 while a portion of the rotation member 47 is fixed to be perpendicular to a plane of the cover 42. When the chamber 41 rotates about the vertical rotation axis of the rotation member 47 as shown by the circular oriented pair of arrows, a centrifugal force $F_c$ that is applied toward the bottom surface 43 of the chamber 41 is generated. Due to the centrifugal force $F_c$, the entire chamber 41 is pivoted at a connection of the rotation member 47 with the chamber 41, and is repositioned such that the upper portion of the chamber 41 is horizontal with the bottom surface 43 of the chamber 41. That is, the magnet 44 is between the chamber 41 and the rotation axis.

Due to the centrifugal force $F_c$, the target cells 17 and the other cells 16 contained in the sample 46 are forced to move toward the bottom surface 43 of the chamber 41, e.g., in a first direction to the right in FIG. 5B. Since the magnet 44 is disposed at the upper portion of the chamber 41, a magnetic force $F_M$ that is applied toward the rotation member 47 at the upper portion of the chamber 41, e.g., in a second direction which is opposite to the centrifugal force $F_c$, exists in the chamber 41. The target cells 17 marked with the magnetic particles 18 are forced to move toward the magnet 44 by the magnetic force $F_M$. If the magnetic force $F_M$ is greater than the centrifugal force $F_c$, the target cells 17 marked with the magnetic particles 18 are pulled by the magnetic force $F_M$ to move toward the magnet 44 of the chamber 41 as shown in FIG. 5B. On the other hand, the other cells 16 which are not influenced by the magnetic force $F_M$ move to the bottom surface 43 of the chamber 41 by the centrifugal force $F_c$ as shown in FIG. 5B. According to the present embodiment, the target cells 17 may be separated from the other cells 16 by using the magnetic force $F_M$ applied in the opposite direction of the centrifugal force $F_c$ as described above. Thus, a separation ratio of the target cells 17 may be increased, and false-positiveness caused by the other cells 16 may be reduced. In addition, with the increase in the separation ratio of the target cells 17, a washing process is not required, and thus cell loss or cell lysis caused by the washing may be reduced or effectively prevented.

Figure 6:
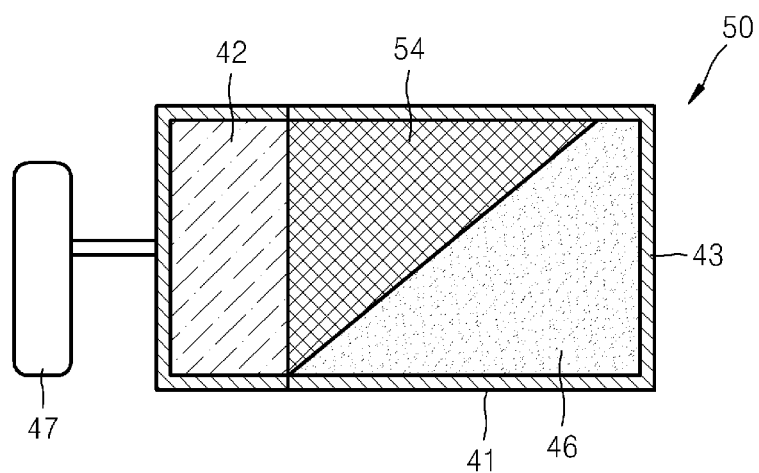
FIG. 6 schematically illustrates another embodiment of a cell separation device, according to the present invention.

FIG. 6 schematically illustrates another embodiment of a cell separation device 50 according to the present invention. The cell separation device 50 shown in FIG. 6 has the same configuration as the cell separation device 40 shown in FIG. 5A, except for the shape of the magnet. In other words, as shown in FIG. 6, the cell separation device 50 has a magnet 54 that has a sloping side in direct contact with the sample 46. Thus, since a surface area of the magnet 54 facing the sample 46 is increased, the magnetic force $F_M$ applied to the target cells 17 marked with the magnetic particles 18 may increase, and more target cells 17 may gather on the surface of the magnet 54 when the centrifugal force $F_c$ and the magnetic force $F_M$ are simultaneously applied to the chamber 41 having the sample 46 therein.

Figure 7:
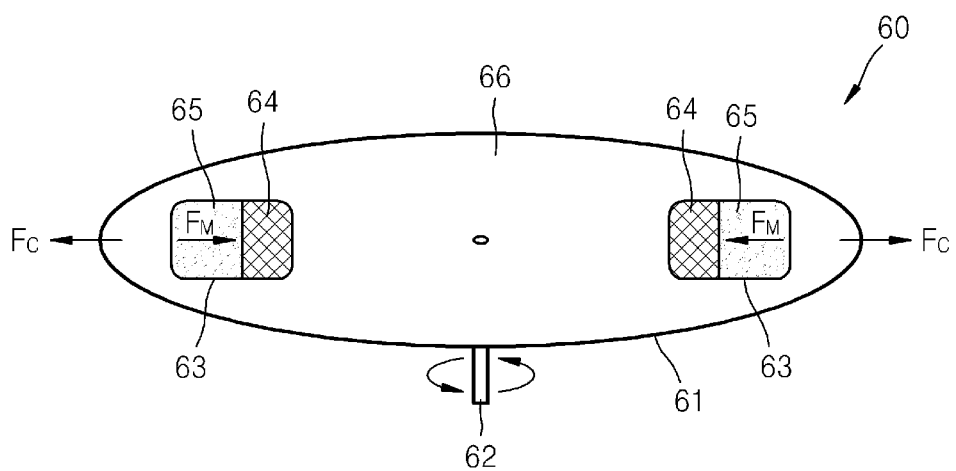
FIG. 7 schematically illustrates another embodiment of a cell separation device, according to the present invention.

FIG. 7 schematically illustrates another embodiment of a cell separation device 60 according to the present invention. The cell separation device 60 shown in FIG. 7 includes a disc 61 that rotates with respect to a central rotation axis 62, at least one chamber 63 that is disposed on an upper surface 66 of the disc 61 and contains a sample 65, and a magnet 64 that is disposed in the chamber 63. According to the present embodiment, the configurations of the chamber 63 and the magnet 64 are the same as those of the chamber 41 and the magnets 44 and 54 shown in FIGS. 5A and 6. In other words, the chamber 41 and the magnets 44 and 54 shown in FIGS. 5A and 6 may be disposed on the disc 61 shown in FIG. 7.

The chamber 63 may be disposed on the disc 61 such that a lengthwise direction of the chamber 63 is identical to a radial direction of the disc 61. In addition, the magnet 64 may be disposed close to (e.g., adjacent to) the rotation axis 62 of the disc 61 within the chamber 63. Although FIG. 7 shows two of the chamber 63, more or less than two of the chambers 63 may be disposed on the disc 61 at equal intervals according to an azimuth angle. In this structure, if the disc 61 rotates, a centrifugal force $F_c$ that is applied toward an outer edge of the disc 61 is generated. Since the magnet 64 is disposed in the chamber 63 close to the rotation axis 62 of the disc 61, the direction of the magnetic force $F_M$ generated by the magnet 64 is opposite to that of the centrifugal force $F_c$. Accordingly, the target cells and the other cells which are contained in the sample 65 may be separated from each other in the cell separation device 60, based on the same principles of the cell separation devices 40 and 50 shown in FIGS. 5A and 6. Accordingly, a separation ratio of the target cells may be increased, and false-positiveness caused by the other cells may be reduced. In addition, with the increase in the separation ratio of the target cells, a washing process is not required, and thus cell loss or cell lysis caused by the washing may be reduced or effectively prevented.

Figure 8:
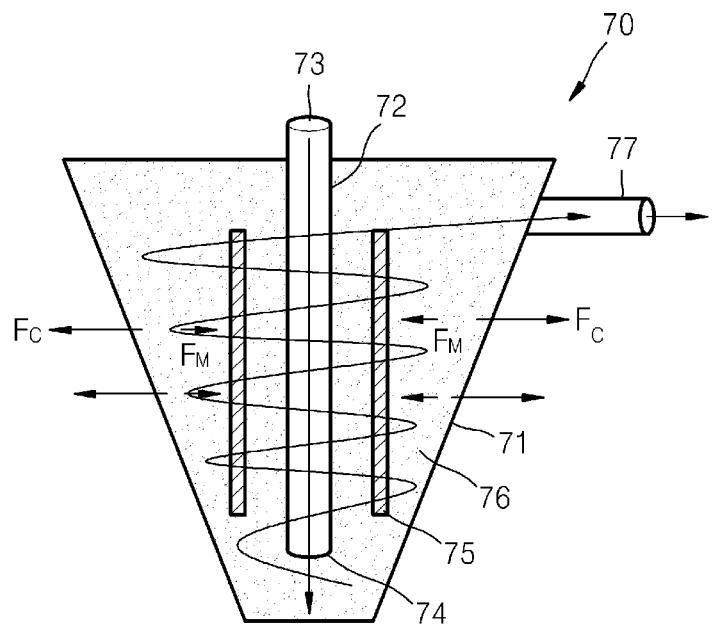
FIG. 8 schematically illustrates another embodiment of a cell separation device, according to the present invention.

FIG. 8 schematically illustrates another embodiment of a cell separation device 70 according to the present invention. Referring to FIG. 8, the cell separation device 70 includes a conic chamber 71 that has a relatively wide top surface and a relatively narrow bottom surface, a sample supply tube 72 that is disposed at a central region of the chamber 71 and penetrates the top surface of the chamber 71, and a magnet 75 that is disposed in the chamber 71 to surround the sample supply tube 72. The conic chamber 71 has a sloping side, and a sample outlet 77 is connected to an upper portion of the sloping side. In addition, a first end of the sample supply tube 72 protrudes from the top surface of the chamber 71 and may function as a sample inlet 73. A second end 74 of the sample supply tube 72 opposite to the first end 73, is disposed to be close to the bottom surface of the chamber 71, and may be separated from the bottom surface of the chamber 71. Two of the magnet 75, are illustrated in FIG. 8. As shown in FIG. 8, the magnets 75 are shown as bar-shaped, to illustrate cross-sections of the magnets 75. The magnet 75 may be a cylindrical magnetic that surrounds the sample supply tube 72 when the cell separation device 70 is viewed along the sample supply tube 72. Accordingly, a separation ratio of the target cells may be increased, and false-positiveness caused by the other cells may be reduced. In addition, with the increase in the separation ratio of the target cells, a washing process is not required, and thus cell loss or cell lysis caused by the washing may be reduced or effectively prevented.

In this structure, a sample 76 is supplied to the chamber 71 via the sample supply tube 72. In particular, the sample 76 is supplied to the chamber 71 from the sample inlet 73 of the upper first end of the sample supply tube 72 to the second end 74 of the sample supply tube 72. The sample 76 initially completely fills the chamber 71 from the relatively narrow lower portion of the chamber 71 to the relatively wide upper portion of the chamber 71, and is then finally discharged out of the chamber 71 via the sample outlet 77 disposed at the upper side of the chamber 71.

In this process, the sample 76 rotates in the conic chamber 71 like a cyclone from the center of the sample supply tube 72. Thus, the centrifugal force $F_c$ is applied to the cells contained in the sample 76 toward an outer direction of the chamber 71. Since the magnet 75 is disposed at a center area of the chamber 71, the magnetic force $F_M$ is applied to the target cells marked with magnetic particles in the opposite direction to the centrifugal force $F_c$. If the magnetic force $F_M$ is greater than the centrifugal force $F_c$, the target cells marked with the magnetic particles are pulled by the magnetic force $F_M$ and gather around the magnet 75 disposed at the center of the chamber 71. On the other hand, the other cells that are not influenced by the magnetic force $F_M$ rotate in the chamber 71 and are discharged out via the sample outlet 77. Thus, the target cells and the other cells which are mixed within the sample 76 may be separated from each other when the centrifugal force $F_c$ and the magnetic force $F_M$ are simultaneously applied to the chamber 71 having the sample 76 therein.

Figure 9A:
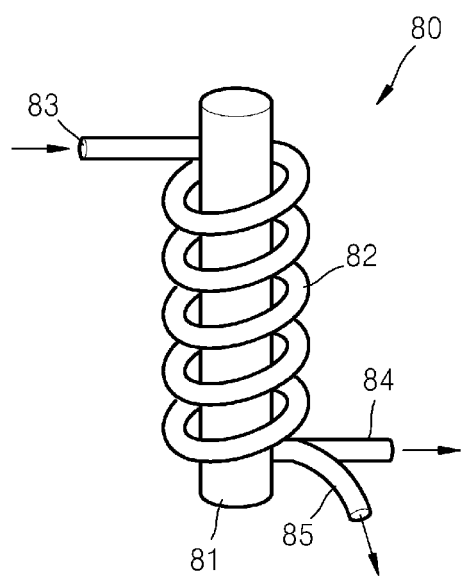
FIG. 9A schematically illustrates another embodiment of a cell separation device, according to the present invention.

FIG. 9A schematically illustrates another embodiment of a cell separation device 80 according to the present invention.

Referring to FIG. 9A, the cell separation device 80 includes a cylindrical magnet 81, a channel 82 that helically winds around the magnet 81, a sample inlet 83 that is connected to a first end of the channel 82, and a first sample outlet 84 and a second sample outlet 85 which are respectively connected to a second end of the channel 82 opposite the first end. In one embodiment, for example, the channel 82 may be a cylindrical tube winding multiple times around the magnet 81. According to the present embodiment, a cross-sectional diameter of the channel 82 may be greater than a diameter of the cells contained in a sample 86 by at least 20 times in order to prevent the cells in the sample 86 (FIG. 9B) from moving along both edges of the channel 82 due to the Dean drag force. The sample inlet 83, the first sample outlet 84 and the second sample outlet 85 are in fluid communication with the channel 82, and collectively form a continuous, single and unitary indivisible fluid path with the channel 82.

Figure 9B:
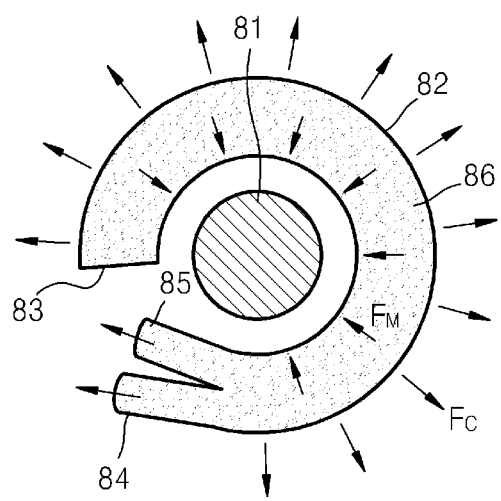
FIG. 9B is a diagram for explaining a principle of separating target cells from other cells in the cell separation device of FIG. 9A.

In this structure, the sample 86 is supplied to the channel 82 via the sample inlet 83 that is connected to the upper first end of the channel 82. Then, the sample 86 naturally flows downward, e.g., from an upper end of the magnet 81 to a lower end of the magnet 81 in the view of FIG. 9A. Since the channel 82 is helically wound around the magnet 81, the sample 86 rotates around the magnet 81 while flowing in the channel 82. Thus, a centrifugal force $F_c$ that is generated by the rotation of the channel 82 around the magnet 81 is applied to the cells contained in the sample 86 toward an outer direction of the chamber 82 as shown in FIG. 9B. Since the magnet 81 is disposed at the center of the chamber 82, the magnetic force $F_M$ is applied to the target cells marked with magnetic particles in the opposite direction to the centrifugal force $F_c$. If the magnetic force $F_M$ is greater than the centrifugal force $F_c$, the target cells marked with the magnetic particles are pulled by the magnetic force $F_M$ and move along an inner edge of the channel 82 close to the magnet 81. On the other hand, the other cells that are not influenced by the magnetic force $F_M$ move along an outer edge of the channel 82 due to the centrifugal force $F_c$.

Thus, when the sample 86 is discharged out of the cell separation device 80 via the lower end of the channel 82, the target cells marked with the magnetic particles are discharged via the second sample outlet 85 connected to the inner edge of the channel 82. The other cells are discharged via the first sample outlet 84 connected to the outer edge of the channel 82. According to the present embodiment, the target cells and the other cells which are mixed in the sample 86 may be separated from each other when the centrifugal force $F_c$ and the magnetic force $F_M$ are simultaneously applied to the chamber 81 having the sample 86 therein. Accordingly, a separation ratio of the target cells may be increased, and false-positiveness caused by the other cells may be reduced. In addition, with the increase in the separation ratio of the target cells, a washing process is not required, and thus cell loss or cell lysis caused by the washing may be reduced or effectively prevented.

A device and method of separating cells by using a magnetic force are described above. It should be understood that the embodiments described herein should be considered in a descriptive sense only and not for purposes of limitation. Descriptions of features or aspects within each embodiment should typically be considered as available for other similar features or aspects in other embodiments.

What is claimed is:

1. A cell separation device comprising:
    a channel having a curved shape in a plan view, and in which a sample flows, the sample comprising target cells marked with magnetic particles, and non-target cells;
    a sample inlet connected to a first end of the channel;
    a first sample outlet and a second sample outlet respectively connected to a second end of the channel opposite the first end; and
    a magnet adjacent to an outer circumference of the channel, the magnet being configured to generate a magnetic force with respect to the sample,
    wherein the magnet is disposed opposite a central region of a curvature of the channel in the plan view such that the magnetic force is substantially opposite an inertial force generated when the sample flows in the curved channel.

2. The device of claim 1, wherein the channel has a circular or oval shape in the plan view.

3. The device of claim 1, wherein the channel has a spiral shape which is a planar curve emanating from a central point, and becoming progressively farther away from the central point as the channel revolves around the central point.

4. The device of claim 3, wherein
    the sample inlet is connected to the first end of the channel at the central point, and
    the first and second sample outlets are connected to the second end of the channel at an outer point of the spiral shape.

5. The device of claim 1, wherein the magnet comprises a single continuous and unitary circular magnet which parallels the outer circumference of the channel.

6. The device of claim 1, wherein an inner distance within the channel is greater than a diameter of cells contained in the sample which flows in the channel by about 2 to about 20 times.

7. The device of claim 1, wherein the magnetic force generated by the magnet is greater than the inertial force.

8. A cell separation device comprising:
    a chamber in which a sample moves, the sample comprising target cells marked with magnetic particles, and non-target cells;
    a magnet at an upper portion inside of the chamber, the magnet being configured to generate a magnetic force with respect to the sample; and
    a rotation member aligned on a rotation axis and connected to the outside of the upper portion of the chamber,
    wherein
    the rotation member is disposed closer to the magnet at the upper portion of the chamber, and farther from a bottom surface of the chamber,
    the magnetic force generated by the magnet is greater than a centrifugal force generated while the chamber rotates with respect to the rotation axis, and
    the magnet is disposed such that the magnetic force and the centrifugal force are substantially opposite each other.

9. The device of claim 8, wherein the magnet includes a protective coating on an outer surface thereof, and between the magnet and the sample within the chamber.

10. The device of claim 8, wherein the magnet has a sloping side in contact with the sample.

11. A cell separation device comprising:
    a disc which rotates with respect to a central rotation axis;
    at least one chamber on an upper surface of the disc, and in which a sample moves, the sample comprising target cells marked with magnetic particles, and non-target cells; and
    a magnet in the at least one chamber, the magnet being configured to generate a magnetic force with respect to the sample,
    wherein
    the magnet is between the sample and the rotation axis of the disc, the magnetic force generated by the magnet is greater than a centrifugal force generated in the at least one chamber when the disc rotates with respect to the central rotation axis, and the magnet is disposed such that the magnetic force and the centrifugal force are substantially opposite each other.

12. The device of claim 11, wherein a lengthwise direction of each of the at least one chamber is aligned with a radial direction of the disc.

13. The device of claim 11, wherein the at least one chamber comprises a plurality of chambers which are disposed on the disc at equal intervals according to an azimuth angle.

14. A cell separation device comprising:
a chamber in which a sample flows, the sample comprising target cells marked with magnetic particles, and non-target cells;
a sample supply tube which penetrates a top surface of the chamber, and is disposed within the chamber;
a magnet within the chamber and adjacent to opposing outer surfaces of the sample supply tube, the magnet being configured to generate a magnetic force with respect to the sample; and
a sample outlet connected to an upper side of the chamber, wherein
the magnetic force generated by the magnet is greater than a centrifugal force generated when the sample rotates in the chamber with respect to the sample supply tube,
the magnet is a cylindrical magnet which surrounds the sample supply tube, and
the magnet is disposed such that the magnetic force and the centrifugal force are substantially opposite each other.

15. The device of claim 14, wherein the chamber has a conical shape with a sloping side, the conical shape having a top surface which is wider than a bottom surface.

16. The device of claim 14, wherein the sample supply tube comprises:
a first end which protrudes from the top surface of the chamber, and is a sample inlet into which the sample is introduced, and
a second end adjacent to a bottom surface of the chamber.

17. The device of claim 16, wherein the sample supply tube is at a central region of the chamber.

18. A cell separation device comprising:
a magnet;
a channel which helically winds around the magnet and in which a sample flows, the sample comprising target cells marked with magnetic particles, and non-target cells, the magnet generating a magnetic force with respect to the sample;
a sample inlet connected to a first end of the channel; and
a first sample outlet and a second sample outlet respectively connected to a second end of the channel opposite the first end,
wherein
the magnetic force generated by the magnet is greater than a centrifugal force generated when the sample flows in the helical channel and rotates around the magnet,
the sample inlet is disposed at an upper end of the magnet and the first and second sample outlets are disposed at a lower end of the magnet, and
the magnet is disposed such that the magnetic force and the centrifugal force are substantially opposite each other.

19. The device of claim 18, wherein the channel is a cylindrical tube winding multiple times around the magnet.

20. The device of claim 19, wherein a diameter of the channel is greater than a diameter of cells contained in the sample by at least 20 times.

* * * * *